United States Patent
Majeed et al.

(10) Patent No.: US 7,842,842 B1
(45) Date of Patent: Nov. 30, 2010

(54) HYDRO-ALKOXYL CITRONELLAL COMPOUNDS—SYNTHETIC ROUTES, COMPOSITIONS AND USES THEREOF

(75) Inventors: Muhammed Majeed, Piscataway, NJ (US); Kalyanam Nagabhushanam, Piscataway, NJ (US); Sakthivel Palaniappan, Banaglore (IN); Ambady Rajagopalan, Bangalore (IN); Rajasekharan Parthasarathy, Bangalore (IN); Kiran Trineshwaraiah-Sirsalmath, Bangalore (IN)

(73) Assignee: Sami Labs Ltd., Bangalore (IN)

( * ) Notice: Subject to any disclaimer, the term of this patent is extended or adjusted under 35 U.S.C. 154(b) by 0 days.

(21) Appl. No.: 12/543,982

(22) Filed: Aug. 19, 2009

(51) Int. Cl.
  C07C 47/00 (2006.01)
  A61K 8/18 (2006.01)
(52) U.S. Cl. .................. 568/496; 512/27
(58) Field of Classification Search ........... 568/496; 512/27
  See application file for complete search history.

(56) References Cited

U.S. PATENT DOCUMENTS 5,288,702 A * 2/1994 Ogura et al. ............ 512/24

FOREIGN PATENT DOCUMENTS

GB   1013459   * 12/1965

OTHER PUBLICATIONS

Henrick et al. Stereoselective Synthesis of Alkyl (2E,4E)- and (2Z, 4E)-3,7,11-Trimethyl-2,4-dodecadienoates. Insect Growth Regulators with Juvenile Hormone Activity. Journal of Organic Chemistry, 1975, vol. 40 (1), p. 1-7.*

* cited by examiner

*Primary Examiner*—Sikarl A Witherspoon

(57) ABSTRACT

Disclosed are new chemical entities 2, 3, 7-trimethyl-7-alkoxy-octanals, represented by the general structure (STR#GEN) wherein "R" represents an alkyl, allyl, alkenyl, or aryl alkyl groups. In specific the present invention discloses novel hydro-alkoxyl citronellal compounds represented by STR#I, II and III to generate new flavor and/or aroma materials. The use of compounds of the present invention as a part of perfume and aroma (fragrance) compositions is also disclosed by the invention.

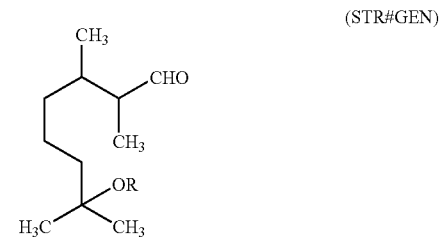

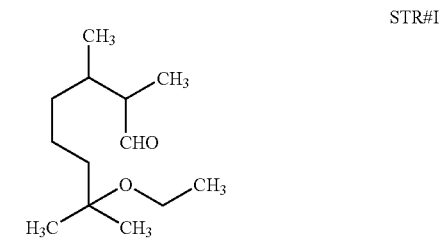

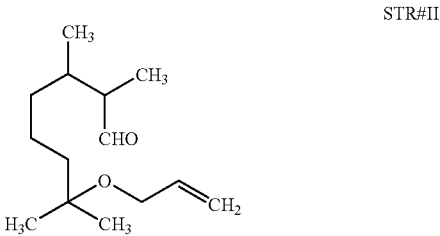

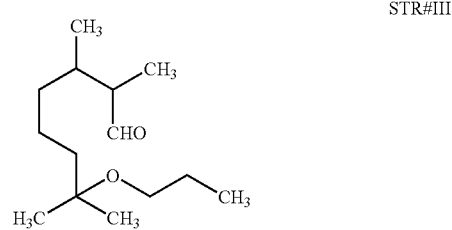

6 Claims, No Drawings

HYDRO-ALKOXYL CITRONELLAL COMPOUNDS—SYNTHETIC ROUTES, COMPOSITIONS AND USES THEREOF

BACKGROUND OF INVENTION

1. Field of Invention

The invention in general relates to flavor and aroma materials. More specifically, the present invention relates to novel hydro-alkoxyl citronellal compounds to generate new flavor and/or aroma materials (compositions).

2. Description of Prior Art

Hydroxycitronellal is a valuable perfume or fragrance, widely used in soap and cosmetic perfumery. Paul Z. Bedonkian, perfumery and flavoring synthesis, second edition, 7967, page 782, refers to it as "an indispensable ingredient in most perfume compositions"

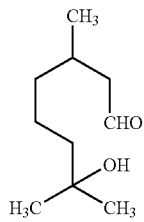

Hydroxycitronellal

Hydroxycitronellal is colorless oily or viscous liquid. Sp.Gr.0.93.B.P.241° C. Very slightly soluble in water, soluble in alcohol and oils. It is poorly soluble in mineral oil and glycerin or propylene glycol.

The present inventors have discovered that novel perfume compositions and perfumed articles and colognes having particularly those possessing a fine herbal and floral aroma, useful as fragrances suitable for incorporation in fine fragrances, cosmetics, toiletries and related applications could be produced by incorporating new structural features not hitherto reported onto the hydroxycitronellal. These compounds are in general called 2,3,7-trimethyl-7-alkoxy-octanal (STR#GEN) and in exemplary embodiments of the present invention represented as STR#I, STR#II and STR#III for purposes of illustration. The invention also provides a novel, economical and commercially viable process from readily available and low cost raw materials for preparing these compounds.

It is the principle objective of the present invention to disclose novel perfume compositions and perfumed articles and colognes having particularly those possessing a fine herbal and floral aroma, useful as fragrances suitable for incorporation in fine fragrances, cosmetics, toiletries and related applications could be produced by incorporating new structural features not hitherto reported onto the hydroxycitronellal.

The present invention fulfills the aforesaid objective and provides further related advantages.

SUMMARY OF THE INVENTION

The present invention discloses new chemical entities in general called 2, 3,7-trimethyl-7-alkoxy-octanals and represented by the structure STR#GEN. More specifically, the present invention relates to the novel hydro-alkoxyl citronellal compounds represented as STR#I, STR#II and STR#III to generate new flavor and/or aroma materials. The novel compounds and synthetic routes thereof are disclosed.

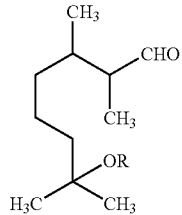

(STR#GEN)

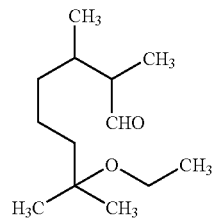

STR#I

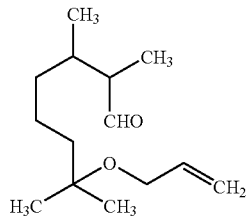

STR#II

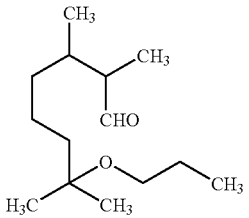

STR#III

DETAILED DESCRIPTION OF THE MOST PREFERRED EMBODIMENT

In the most preferred embodiment, the present invention relates to new chemical entities in general called 2,3,7-trimethyl-7-alkoxy-octanals and represented by the structure STR#GEN wherein "R" represents an alkyl, allyl, alkenyl, or aryl alkyl groups. In exemplary embodiments, the present invention relates to the novel hydro-alkoxyl citronellal compounds (new chemical entities) represented as STR#I, STR#II and STR#III to generate new flavor and/or aroma materials. In yet another preferred embodiment, the present invention discloses the general synthetic scheme (GENERAL SCHEME) for the preparation of new chemical entities in general called 2, 3, 7-trimethyl-7-alkoxy-octanals and represented by the structure STR#GEN wherein "R" represents an alkyl, allyl, alkenyl, or aryl alkyl groups. More specifically, the aforesaid general scheme is used for the preparation of novel hydro-alkoxyl citronellal compounds represented as STR#I, STR#II and STR#III.

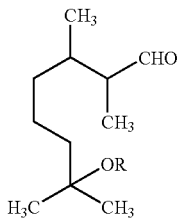

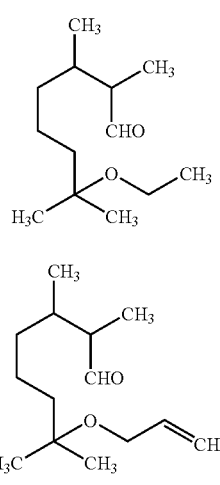

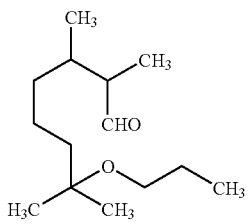

(General Scheme)

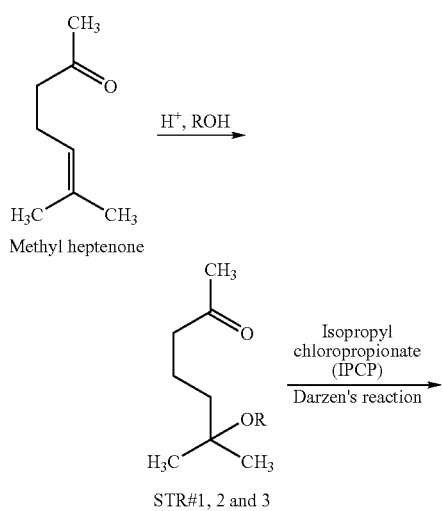

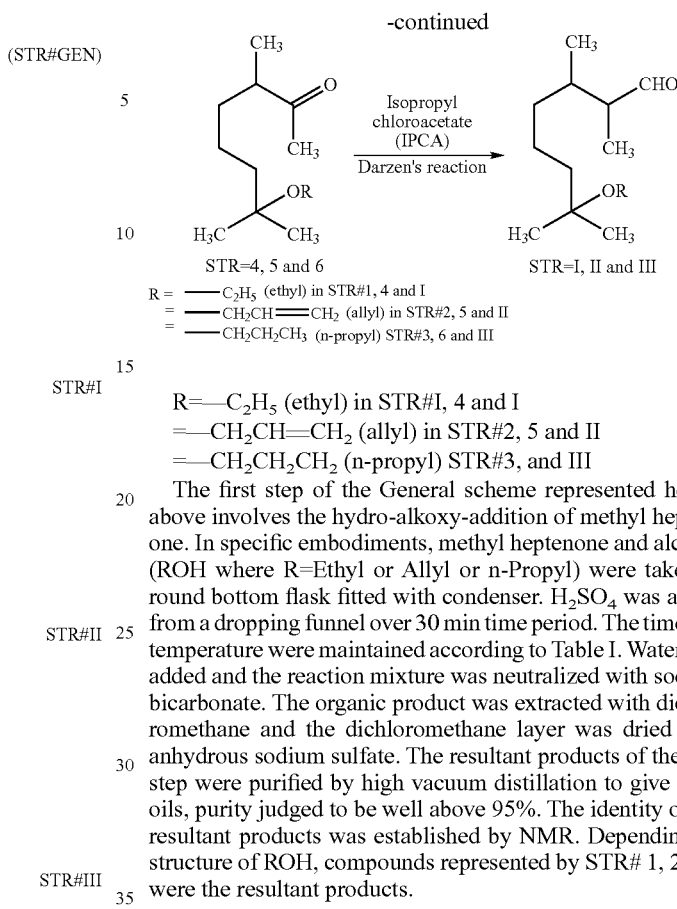

R=—C$_2$H$_5$ (ethyl) in STR#I, 4 and I
=—CH$_2$CH=CH$_2$ (allyl) in STR#2, 5 and II
=—CH$_2$CH$_2$CH$_2$ (n-propyl) STR#3, and III The first step of the General scheme represented herein above involves the hydro-alkoxy-addition of methyl heptenone. In specific embodiments, methyl heptenone and alcohol (ROH where R=Ethyl or Allyl or n-Propyl) were taken in round bottom flask fitted with condenser. H$_2$SO$_4$ was added from a dropping funnel over 30 min time period. The time and temperature were maintained according to Table I. Water was added and the reaction mixture was neutralized with sodium bicarbonate. The organic product was extracted with dichloromethane and the dichloromethane layer was dried over anhydrous sodium sulfate. The resultant products of the first step were purified by high vacuum distillation to give clear oils, purity judged to be well above 95%. The identity of the resultant products was established by NMR. Depending on structure of ROH, compounds represented by STR# 1, 2 or 3 were the resultant products.

TABLE I

| Structure | Amount of methyl-heptenone (gram) | Amount of Alcohol (ml) | Eq of Acid | Temperature (° C) | Time (hours) | Yield (%) |
| --- | --- | --- | --- | --- | --- | --- |
| 1 | 100 | 300 (Ethyl alcohol) | 0.24 | 60-65 | 22 | 09.9 |
| 2 | 100 | 300 (Allyl alcohol) | 3.50 | 60-65 | 17 | 10.2 |
| 3 | 100 | 400 (n-Propanol) | 0.20 | 60-65 | 14 | 17.2 |

In alternative embodiments, it is possible to use any alcohol for the hydro-alkoxy-addition of methyl heptanone. Thus a variety of related structures that serve as starting materials for several useful fragrance material end products may be obtained in the first step.

The second step of the general scheme represented herein above includes compounds represented by STR#1, 2 or 3 as starting materials. In specific embodiments, sodium and isopropyl alcohol were taken in a round bottomed flask fitted with a condenser. The mixture was refluxed so that sodium dissolved completely. The reaction mixture was cooled to 0° C., and a mixture containing isopropyl chloropropionate (IPCP) and compounds represented by STR# 1, 2 or 3 was added at 0° C. over a period of 30 minutes under stirring (Darzen's reaction). The time and temperature were maintained as described in Table II to give a glycidic ester which was isolated and identified by GC/mass spectra. This glycidic ester was cooled to 0° C. and sodium hydroxide solution was added over 30 minutes. The reaction was warmed slowly to room temperature under stirring. The pH was adjusted to 6-7 by adding acetic acid and extracted with dichloromethane (3×100 ml) for removing impurities. The pH was gain adjusted to 5 using acetic acid. The aqueous layer was extracted with dichloromethane and dried over sodium sulfate. The solvent was removed and the product was purified by vacuum distillation. The resultant products of the second step included compounds of the STR# 4, 5 or 6 depending on the starting compounds represented by STR# 1, 2 or 3 respectively. The structures of compounds represented by STR# 4, 5 or 6 were confirmed by IR and NMR data.

TABLE II

| Structure | Amount of S-I (gram) | Eq of IPCP | Temperature (° C.) | Time (hours) |
|---|---|---|---|---|
| 4 | 10 of compound represented by STR#1 | 1.4 | 0-5 | 08 |
| 5 | 10 of compound represented by STR#2 | 1.4 | 0-5 | 08 |
| 6 | 10 of compound represented by STR#3 | 1.4 | 0-5 | 10 |

The third step of the general scheme represented herein above includes compounds represented by STR#4, 5 or 6 respectively as starting materials. In specific embodiments, sodium and isopropyl alcohol were taken in a round bottomed flask fitted with a condenser. The mixture was refluxed so that sodium dissolved completely. The reaction mixture was cooled to 0° C., and a mixture containing isopropyl chloroacetate (IPCA) and compounds represented by STR#4, 5 or 6 was added at 0° C. over a period of 30 minutes under stirring (Danzen reaction). The time and temperature were maintained as described in Table III to give a glycidic ester which was isolated and identified by GC/mass spectra. This glycidic ester was cooled to 0° C. and sodium hydroxide solution was added over 30 minutes. The reaction was warmed slowly to room temperature under stirring. The pH was adjusted to 6-7 by adding acetic acid and extracted with dichloromethane (3×100 ml) for removing impurities. The pH was gain adjusted to 5 using acetic acid. The aqueous layer was extracted with dichloromethane and dried over sodium sulfate. The solvent was removed and the product was purified by vacuum distillation. The resultant products of the third step included compounds (new chemical entities) represented by STR# 1, II and III respectively depending on the starting compounds represented by STR# 4, 5 or 6. STR# 1, II and III were confirmed by IR and NMR data.

TABLE III

| Structure | Amount of S-II (gram) | Eq of IPCA | Temperature (° C) | Time (hours) |
|---|---|---|---|---|
| 4 | 5 of compound represented by STR#4 | 1.4 | 0-5 | 10 |
| 5 | 5 of compound represented by STR#5 | 1.4 | 0-5 | 10 |
| 6 | 5 of compound represented by STR#6 | 1.4 | 0-5 | 12 |

The IR and NMR data for STR# 1, II and III are elucidated herein below.

STR# 1

IR: C=O stretching at 1724 cm$^{-1}$; C—O at stretching at 1072 cm$^{-1}$ and C—H at stretching at 2972 cm$^{-1}$ NMR in δ ppm: 21H 0.96-1.38, 1H 1.87, 1H 2.51, 2H 3.41, 1H 9.72. (Whenever multiplets are obtained, the center of the multiplet is given)

STR# II

IR: C=O stretching at 1726 cm$^{-1}$; C—O at stretching at 1066 cm$^{-1}$ and C—H at stretching at 2968 cm$^{-1}$ NMR in δ ppm: 18H, 1.26, 1H 1.87, 1H 2.51, 2H 3.87, 2H 5.24, 1H 5.9, 1H 9.72. (Whenever multiplets are obtained, the center of the multiplet is given)

STR# III

IR: C=O stretching at 1726 cm$^{-1}$; C—O at stretching at 1081 cm$^{-1}$ and C—H at stretching at 2966 cm$^{-1}$ NMR in δ ppm: 23H 0.96-1.38, 1H 1.87, 1H 2.51, 2H 3.41, 1H 9.72. (Whenever multiplets are obtained, the center of the multiplet is given)

Exemplary examples of fragrant formulations prepared using compounds represented by STR# 1, II and III are elucidated herein below. Said formulations are only illustrative and not exhaustive representations.

EXAMPLE I

Table IV

Incorporation of 7-Ethoxy-2,3,7-trimethyl-octanal (STR#I) of the present invention into a perfume composition:

TABLE IV

| Ingredients | % by weight |
|---|---|
| Aldehyde C-9 10% | 40.0 |
| Aldehyde C-11 10% | 20.0 |
| Linalool | 11.0 |
| Iso Butyl Phenyl Acetate | 6.0 |
| Phenyl Ethyl Acetate | 3.5 |
| Geranyl Acetate | 6.0 |
| 7-Ethoxy-2,3,7-trimethyl-octanal | 6.0 |
| Phenyl Ethyl Alcohol | 6.0 |
| Phenylxylylethane | 1.5 |
| Perfume as a whole | 100.0 |

The aforesaid fragrance was found to be a pleasing fragrance with rose notes.

EXAMPLE II

Table V

Incorporation of 7-Allyloxy-2,3,7-trimethyl-octanal (STR#II) of the present invention into a perfume composition:

TABLE V

| Ingredients | % by weight |
|---|---|
| Benzophenone | 01.5 |
| Coumarin | 01.5 |
| Musk xylol | 03.0 |
| Phenyl acetic acid | 01.0 |
| Alpha amyl cinnamic aldehyde | 01.0 |
| Iso butyl phenyl acetate | 01.0 |
| Phenyl ethyl acetate | 00.5 |
| Cyclamen aldehyde | 00.5 |
| Geraniol | 01.0 |
| Benzyl acetate | 02.0 |
| Allyl carpoate | 01.0 |
| Orange oil | 01.0 |
| Lanandin | 04.0 |
| Benzyl propionate | 04.0 |
| Aldehyde C-16 2% (by wt in ethanol) | 03.0 |
| Iso bornyl acetate | 06.0 |
| Rosemary oil | 11.0 |
| 7-Allyloxy-2,3,7-trimethyl-octanal | 01.5 |
| Oil petitgrain | 00.5 |
| Terpineol | 06.0 |
| Geranyl Acetate | 03.0 |
| Phenyl ethyl iso butyrate | 03.0 |
| Aldehyde C-11 1% | 05.0 |
| Methyl acetate | 19.0 |
| Phenylxylylethane | 19.0 |
| Perfume as a whole | 100.0 |

The above fragrance was found to be a pleasing fragrance with lavender note.

EXAMPLE III

Table VI

Incorporation of 2,3,7-trimethyl-7-propoxy-octanal (STR#III) of the present invention into a perfume composition:

TABLE VI

| Ingredients | % by weight |
|---|---|
| Benzophenone | 02.0 |
| Benzopyrone | 02.0 |
| Anisic aldehyde | 05.0 |
| Musk xylol | 07.0 |
| Phenyl Ethyl Acetate | 03.5 |
| Genaryl Acetate | 06.0 |
| 2,3,7-trimethyl-7-propoxy-octanal | 06.0 |
| Phenyl Ethyl Alcohol | 06.0 |
| Indole | 05.0 |
| Phenylxylylethane | 01.5 |
| Geraniol | 05.0 |
| Aldehyde C-9 10% | 30.0 |
| Aldehyde C-11 10% | 10.0 |
| Linalool | 11.0 |
| Perfume as a whole | 100.0 |

The above fragrance was found to be a pleasing fragrance with herbal and floral note.

Illustrative examples presented herein above do not limit the invention. Persons familiar with the art will be able to produce more such examples and such examples are also covered by this invention.

We claim:

1. New chemical entities 2,3,7-trimethyl-7-alkoxy-octanals, represented by the general structure (STR#GEN) wherein "R" represents an alkyl, allyl, alkenyl, or aryl alkyl groups.

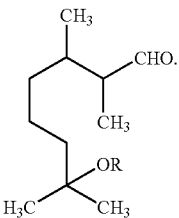

(STR#GEN)

2. New chemical entity 7-Ethoxy-2,3,7-trimethyl-octanal according to claim 1, said entity represented by STR# I.

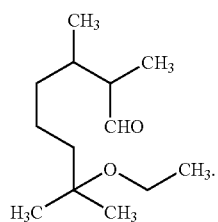

STR#I

3. New chemical entity 7-Allyloxy-2,3,7-trimethyl-octanal according to claim 1, said entity represented by STR# II.

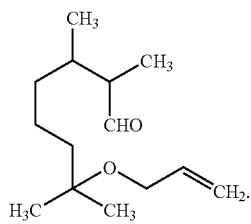

STR#II

4. New chemical entity 2,3,7-trimethyl-7-propoxy-octanal according to claim 1, said entity represented by STR# III.

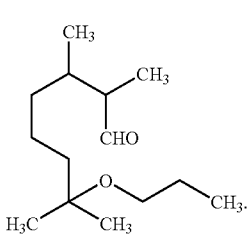

STR#III

5. New chemical entities 2,3,7-trimethyl-7-alkoxy-octanal according to claim 1, wherein said entities are prepared through the steps of:

(i) Alkoxy addition of methyl heptetone with aliphatic, allylic or aryl alkyl alcohols to produce 6-alkoxy-6-methyl heptanone;

(ii) Reacting the 6-Alkoxy-6-methyl heptanone produced in step (i) with isopropylchloropropionate followed by hydrolysis to produce 3,7-Dimethyl-7-alkoxy-2-octanone; and (iii) Reacting the 3,7-Dimethyl-7-alkoxy-2-ocatnones produced in step (ii) with isopropylchloroacetate followed by hydrolysis to produce 2,3,7-trimethyl-7-lkoxy-octanal.

6. A fragrance composition containing 0.5% to 10.0% of 2,3,7-trimethyl-7-alkoxy-octanal represented by the general structure (STR#GEN) and one or more ingredients selected from the group consisting of rosemary oil, methyl acetate, phenylxylylethane, linalool, aldehyde c-9, aldehyde C-11 or geranyl acetate.

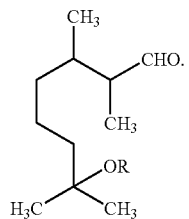

(STR#GEN)

* * * * *